United States Patent [19]

Garner et al.

[11] 4,277,400
[45] Jul. 7, 1981

[54] 2(INDOL-3'-OYL) 3,4,5,6-TETRAHALO BENZOIC ACID ANHYDRIDES

[75] Inventors: Robert Garner, Greenmount; Michael J. Whitehead, Failsworth, both of England

[73] Assignee: Ciba-Geigy Corporation, Ardsley, N.Y.

[21] Appl. No.: 38,024

[22] Filed: May 10, 1979

[30] Foreign Application Priority Data

May 18, 1978 [GB] United Kingdom ............... 20456/78
Apr. 3, 1979 [GB] United Kingdom ............... 11660/79

[51] Int. Cl.³ ............................................ C07D 209/18
[52] U.S. Cl. .................. 260/326.13 B; 260/326.14 R; 252/275
[58] Field of Search .................. 260/326.13 B, 326.14, 260/343.3; 282/27.5

[56] References Cited

U.S. PATENT DOCUMENTS 3,540,911  11/1970  Lin ............................ 260/326.14 R
3,829,322  8/1974  Ozutsumi et al. ........... 260/326.14 R Primary Examiner—Nicholas S. Rizzo
Assistant Examiner—D. B. Springer
Attorney, Agent, or Firm—Edward McC. Roberts; John P. Spitals

[57] ABSTRACT

Anhydride compounds of the formula

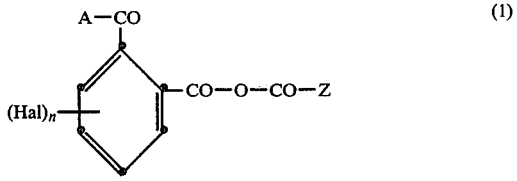

wherein A is an optionally substituted amino-phenyl or optionally substituted 3-indolyl radical, Hal represents halogen, Z represents hydrogen, alkyl of 1 to 4 carbon atoms or an optionally substituted phenyl radical and n is 1 to 4; these anhydrides are particularly useful as starting materials for the manufacture of halogenated 3-aryl-3-indolyl-phthalides or fluoran derivatives.

4 Claims, No Drawings

2(INDOL-3'-OYL) 3,4,5,6-TETRAHALO BENZOIC ACID ANHYDRIDES

This invention relates to novel mixed aromatic anhydrides, their manufacture and their use for the manufacture of asymmetrical 3,3-disubstituted halogenated phthalide compounds and especially of halogenated 3-aryl-3-indolyl-phthalides.

The conventional method of preparing 3-aryl-3-indolyl-phthalides involves the reaction of either a 2-aroyl-benzoic acid with an indole compound or a 2-indol-3'-oyl-benzoic acid with an aryl compound. However, attempts to prepare the corresponding 4,5,6,7-tetrahalogenated compounds result in the simultaneous formation of 3,3-bis-indolyl-phthalides, in many cases this being the major product. It has now surprisingly been found that by using novel mixed anhydrides of said benzoic acids as starting compounds it is possible to obtain halogenated 3-aryl-3-indolyl-phthalides which substantially are free from undesired by-products.

Accordingly the invention relates to novel aromatic mixed anhydrides of the formula

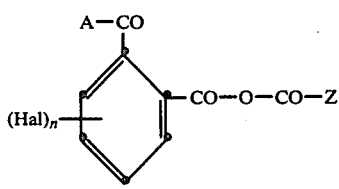

(1)

in which A represents an optionally substituted aminophenyl radical or an optionally substituted 3-indolyl radical, Z represents hydrogen, alkyl of 1 to 4 carbon atoms or an optionally substituted phenyl radical, Hal represents halogen and n is 1 to 4.

These mixed anhydrides may be obtained by reacting a benzoic acid of the formula

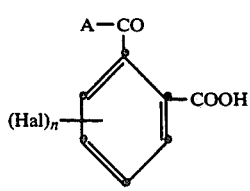

(2)

with an acid anhydride of the formula

(4)

wherein A, Hal, Z and n have the given meanings and Z' is hydrogen, alkyl of 1 to 4 carbon atoms or an optionally substituted phenyl radical.

The anhydrides of the formula (3) may be used as mixed anhydrides that is to say as anhydrides of two different acids.

This reaction may be carried out in an anhydric medium e.g., in excess of the anhydride used such as acetic anhydride or in an organic solvent such as benzene, toluene, xylene, or a chlorobenzene, preferably at temperatures at or below the boiling point of such solvents.

Particularly suitable anhydride compounds correspond to the formula

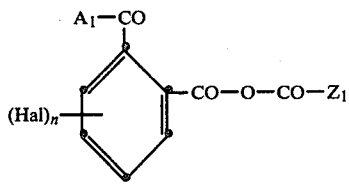

(4)

wherein $A_1$ is an aminophenyl group of the formula

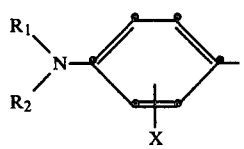

(4a)

or a 3-indolyl radical of the formula

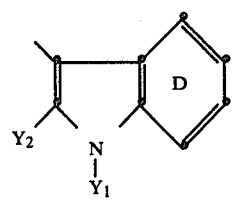

(4b)

wherein $R_1$ and $R_2$ each independently of the other, represent alkyl of 1 to 12 carbon atoms, cycloalkyl, phenyl or benzyl or $R_1$ and $R_2$, together with the nitrogen atom to which they are attached, represent a 5- or 6-membered heterocyclic radical, X represents hydrogen, halogen, lower alkyl or lower alkoxy, $Y_1$ represents hydrogen, alkyl of 1 to 12 carbon atoms, phenyl or benzyl, $Y_2$ represents hydrogen, lower alkyl or phenyl and the ring D is unsubstituted or substituted by halogen, nitro, lower alkyl or lower alkoxy, Hal represents halogen and n is 1 to 4, and $Z_1$ represents hydrogen, alkyl of 1 to 4 carbon atoms or phenyl.

Further preferred mixed anhydrides are, in particular, those having the formula

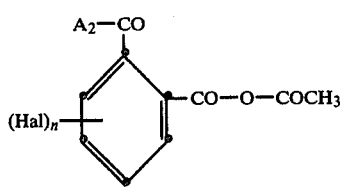

(5)

wherein $A_2$ is an aminophenyl group of the formula

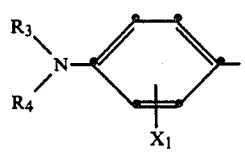

(5a)

or a 3-indolyl radical of the formula

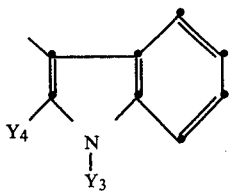

wherein $R_3$ and $R_4$ each independently of the other are lower alkyl, phenyl or benzyl, $X_1$ represents hydrogen, lower alkyl or lower alkoxy, $Y_3$ represents alkyl of 1 to 8 carbon atoms or benzyl, $Y_4$ represents methyl or phenyl, Hal represents halogen and n is 1 to 4.

The mixed anhydrides of the formulae (1), (4) and (5) are valuable intermediate products for the manufacture of said phthalides or of fluoran derivatives which are particularly useful as colour formers in pressure-sensitive or thermoreactive recording materials.

In a further aspect the invention provides a process for the manufacture of halogenated phthalide compounds of the formula

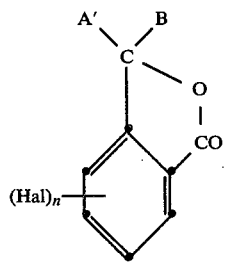

in which of A' and B one represents an optionally substituted aminophenyl radical and the other represents an optionally substituted 3-indolyl radical, Hal represents halogen and n is 1 to 4.

The process is characterised in that an anhydride of the formula

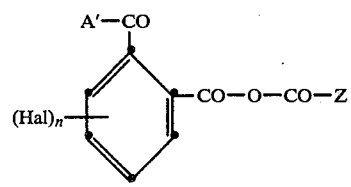

wherein Hal, A' and n have the given meanings and Z represents hydrogen, alkyl of 1 to 4 carbon atoms or an optionally substituted phenyl radical, is reacted with a compound of the formula

 (8)

wherein B has the given meaning.

The amino-phenyl radical represented by A, A' or B may be an optionally substituted p-aminophenyl radical wherein optional substituents may be bound at the nitrogen atom and/or in the benzene ring. Said substituents may be alkyl having 1 to 12 carbon atoms, alkenyl having at most 12 carbon atoms, cycloalkyl, phenyl or benzyl both optionally substituted by halogen, nitro, lower alkyl or lower alkoxy. The benzene ring of said p-amino phenyl radical may also contain halogen, nitro, lower alkyl, lower alkoxy or an additional, optionally substituted, amino group. The indolyl radical represented by A, A' or B may be substituted at the nitrogen and/or at a carbon atom of the heterocycle or in the benzene ring. Said substituents may be alkyl of 1 to 12 carbon atoms, alkenyl having at most 12 carbon atoms, phenyl or benzyl. The benzene ring of the heterocyclic system may also contain halogen, nitro, lower alkyl or lower alkoxy.

Z denotes preferably hydrogen, alkyl of 1 to 4 carbon atoms, phenyl or phenyl substituted by halogen, methyl, methoxy, ethoxy, lower alkylamino or di-lower alkylamino. Halogen in each occurence in the definitions of the substituents preferably stands for fluorine or bromine or especially chlorine.

Valuable halogenated phthalide compounds which can be manufactured by the present process correspond to the formula

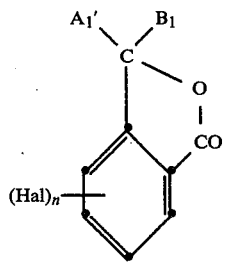

in which of $A_1'$ and $B_1$, one represents an aminophenyl group of the formula

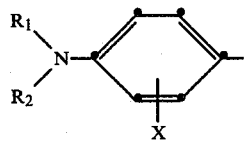

and the other represents a 3-indolyl radical of the formula

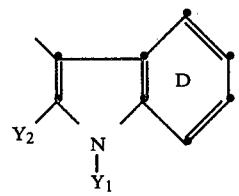

wherein $R_1$ and $R_2$ each independently of the other, represent alkyl of 1 to 12 carbon atoms, cycloalkyl, phenyl or benzyl or $R_1$ and $R_2$, together with the nitrogen atom to which they are attached, represent a 5- or 6-membered heterocyclic radical, X represents hydrogen, halogen, lower alkyl or lower alkoxy, $Y_1$ represents hydrogen, alkyl of 1 to 12 carbon atoms, acetyl, phenyl or benzyl, $Y_2$ represents hydrogen, lower alkyl or phenyl and the ring D is unsubstituted or substituted by halogen, nitro, lower alkyl or lower alkoxy, Hal represents halogen and n is 1 to 4.

The phthalide compounds of the formula (9) are manufactured from the mixed anhydrides and the aminobenzene compounds or indole compounds corresponding to the symbols $A_1'$ and $B_1$. In the anhydridic moiety Z is preferably hydrogen, alkyl of 1 to 4 carbon atoms or phenyl.

In the definition of the radicals of mixed anhydrides of the formulae (1), (4), (5) and (7), the phthalide compounds of the formulae (6) and (9) and of the starting materials of the formulae (2), (3) and (8), lower alkyl and lower alkoxy as a rule represent those groups which contain 1 to 5 and especially 1 to 3 carbon atoms, such as, for example, methyl, ethyl, n-propyl, isopropyl, n-butyl, sec-butyl, tert-butyl or amyl and methoxy, ethoxy or isopropoxy.

If the substituents $R_1$, $R_2$ and $Y_1$ represent alkyl groups, these can be straight-chain or branched alkyl radicals. Examples of such alkyl radicals are methyl, ethyl, n-propyl, isopropyl, n-butyl, sec-butyl, n-hexyl, n-octyl or n-dodecyl. Cycloalkyl represented by the R-radicals is for example cyclopentyl or, preferably, cyclohexyl.

If the substituents $R_1$ and $R_2$, together with the common nitrogen atom, represent a heterocyclic radical, this is, for example, pyrrolidino, piperidino, pipecolino, morpholino, thiomorpholino or piperazino.

The substituents $R_1$ and $R_2$ are preferably benzyl or lower alkyl. The N-substituent $Y_1$ is, in particular, hydrogen, phenyl, benzyl or alkyl with 1 to 8 carbon atoms, for example n-octyl or, above all, methyl or ethyl. The radical $Y_2$ advantageously denotes lower alkyl, especially methyl, or phenyl, X is preferably hydrogen, methyl, methoxy or most preferably ethoxy.

The ring D is preferably not further substituted or is substituted by halogen, lower alkyl or lower alkoxy, for example by chlorine, methyl or methoxy. Phthalide compounds which are important in practice and can advantageously be produced by the present process are of the formula

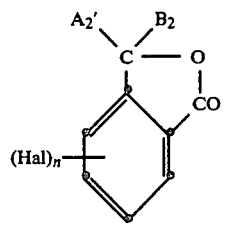

(10)

in which of $A_2'$ and $B_2$ one represents an amino-phenyl group of the formula

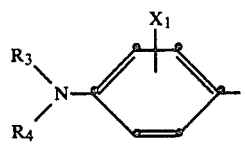

(10a)

and the other represents a 3-indolyl radical of the formula

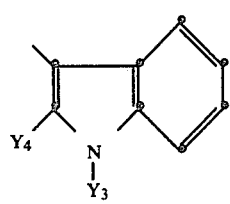

(10b)

wherein $R_3$ and $R_4$ each independently of the other are lower alkyl, phenyl or benzyl, $X_1$ represents hydrogen, lower alkyl or lower alkoxy, $Y_3$ represents alkyl of 1 to 8 carbon atoms or benzyl, $Y_4$ represents methyl or phenyl, Hal represents halogen and n is 1 to 4.

The phthalide compounds of formula (10) are advantageously prepared by reacting an anhydride of the formula

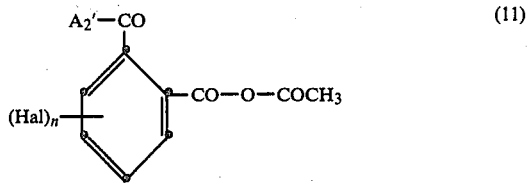

(11)

with a compound of the formula $$B_2-H \quad (12)$$

wherein $A_2'$, $B_2$, Hal and n have the given meanings. Among the anhydrides of the formula (11) 2-(1'-ethyl-2'-methyl-indol-3'-oyl)-3,4,5,6-tetrachloro benzoic acetic anhydride or 2-(4'-diethylamino-2'-ethoxybenzoyl)-3,4,5,6-tetrachloro benzoic acetic anhydride are particularly preferred.

The reaction of the anhydrides of the formula (7) with the compound of formula (8) is advantageously carried out in an organic solvent and at reflux temperature. Such solvent may be any organic solvent which is unreactive towards the reactants or products. It is preferably a cycloaliphatic or aromatic hydrocarbon such as cyclohexane, benzene, toluene or xylene. The best results in respect of yield and purity of the resulting phthalides are achieved with toluene as the most preferred solvent. It is appropriate to use a temperature ranging from 60° C. to 150° C. The reaction time depends on the solvent and temperature and is as a rule between ½ and 10 hours.

The phthalide compounds obtained according to the process of the invention are isolated, and purified, by known methods. A great advantage of the novel method is that it can readily be utilised industrially and gives pure end products in very good yields.

The halogenated 3-aminophenyl-3-indolyl-phthalides of the formulae (6), (9) and (10) are usually colourless or slightly coloured. However, they give intense blue or green shades when they are brought into contact with a developer, that is to say, an electron acceptor such as attapulgite clay, silton clay or a phenolformaldehyde resin. They are suitable as colour formers for use in a heat or pressure-sensitive recording material, which can be either copying material or documenting material. They may also be used as intermediate products for the manufacture of a further class of colour formers for example by reaction of said halogenated phthalides with an amino compound of the formula

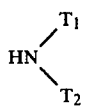

wherein $T_1$ represents alkyl of at most 12 carbon atoms which is unsubstituted or substituted by halogen, hydroxyl, cyano, lower alkoxy or lower alkylcarbonyloxy; cycloalkyl, phenyl, benzyl or phenyl or benzyl which are substituted by halogen, nitro, lower alkyl or lower alkoxy and $T_2$ represents hydrogen, alkyl of at most 12 carbon atoms, which is unsubstituted or substituted by halogen, hydroxyl, cyano, lower alkoxy or lower alkyl-carbonyloxy; cycloalkyl, benzyl or benzyl which is substituted by halogen, nitro, lower alkyl or lower alkoxy, and $T_2$ may also represent acyl having 1 to 8 carbon atoms or $T_1$ and $T_2$ together with the nitrogen atom to which they are attached independently represent a 5- or 6-membered, preferably saturated, heterocyclic radical such as pyrrolidino or piperidino.

In the Examples which follow, percentages are percentages by weight.

EXAMPLE 1

(a) A mixture of 14.5 g 2-(1'-ethyl-2'-methyl-indol-3'-oyl)-3,4,5,6-tetrachloro-benzoic acid [1-ethyl-2-methyl-3-(2'-carboxy-3',4',5',6'-tetrachloro-benzoyl)-indole] and 15 ml acetic anhydride is heated at 120° C. for 24 hours. Afterwards the precipitated solid is filtered off at 120° C., washed with methanol and dried at 60° C. in vacuo to give a product which after crystallization from methanol and then diethyl ether, yields 6,32 g of the mixed anhydride of the formula

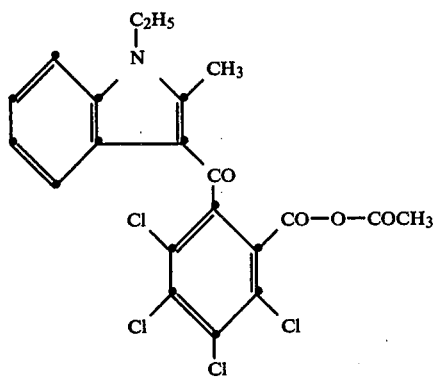

as a white solid having a melting point of 198° C. (b) A mixture of 2,43 g 2-(1'-ethyl-2'-methyl-indol-3'-oyl)-3,4,5,6-tetrachlorobenzoic acetic anhydride of formula (21), 0,96 g N,N-diethyl-m-phenetidin and 5 ml toluene is heated at reflux for 16 hours. The toluene is distilled off under reduced pressure and the residue is slurried with 5 ml methanol over night to give a precipitate. This is filtered off, washed with methanol and dried at 60° C. in vacuo to yield 1,94 g (62% of the theory) of the phthalide compound of the formula

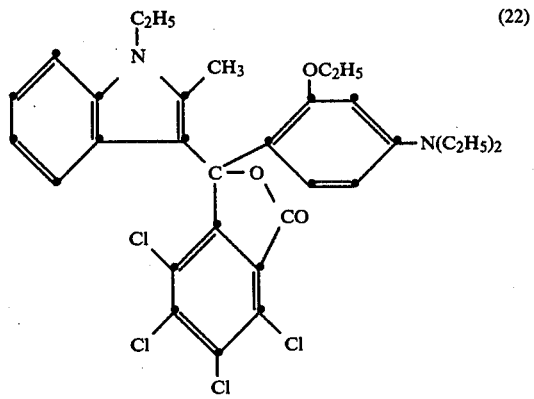

This phthalide compound has a melting point of 189° to 190° C. and is chromatographically and analytically pure.

EXAMPLE 2

(a) A mixture of 8.0 g 2-(4'-diethylamino-2'-ethoxybenzoyl)-3,4,5,6-tetrachlorobenzoic acid and 15 ml acetic anhydride is heated at 120° C. for 24 hours. The reaction mixture is filtered off, washed with methanol and dried at 60° C. in vacuo to yield 1.7 g of a mixed anhydride of the formula

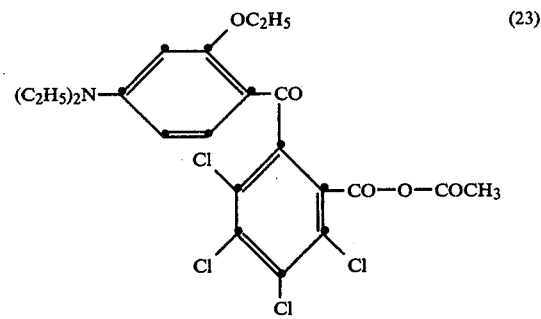

as a white solid, m.p. 141° to 142° C.

(b) By a similar procedure as described in Example 1 (b) but using as reactants 0,26 g of the anhydride of formula (23) and 0,08 g 1-ethyl-2-methylindole in 3 ml toluene instead of the anhydride of formula (21) and N,N-diethyl-m-phenetidine, 0,21 g corresponding to 67,7% of the theory, of the same phthalide product of formula (22) m.p. 188° to 190° C., is obtained.

What we claim is:

1. An anhydride compound of the formula

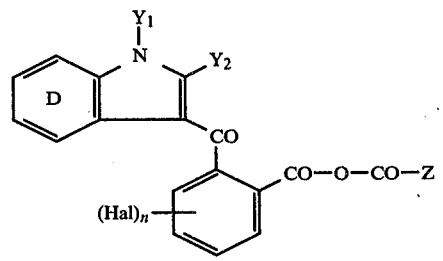

wherein
Hal is fluoro, bromo or chloro,
n is 1 to 4,
Z is alkyl of 1 to 4 carbon atoms, phenyl or phenyl substituted by fluoro, bromo, chloro, methyl, methoxy, ethoxy, alkylamino of 1 to 5 carbon atoms or dialkylamino with 1 to 5 carbon atoms in each alkyl group.
$Y_1$ is hydrogen, alkyl of 1 to 12 carbon atoms, phenyl or benzyl,
$Y_2$ is hydrogen, alkyl of 1 to 5 carbon atoms or phenyl,
and the ring D is unsubstituted or substituted by fluoro, bromo, chloro, nitro, alkyl of 1 to 5 carbon atoms or alkoxy of 1 to 5 carbon atoms.

2. An anhydride of claim 1, wherein Z is alkyl of 1 to 4 carbon atoms or phenyl.

3. An anhydride of claim 1 wherein Z is methyl, $Y_1$ is alkyl of 1 to 8 carbon atoms or benzyl and $Y_2$ is methyl or phenyl.

4. 2-(1'-ethyl-2'-methyl-indol-3'-oyl)-3,4,5,6-tetrachloro-benzoic acetic anhydride.

* * * * *